US008633194B2

(12) United States Patent
Fanara et al.

(10) Patent No.: US 8,633,194 B2
(45) Date of Patent: Jan. 21, 2014

(54) PHARMACEUTICAL COMPOSITION OF PIPERAZINE DERIVATIVES

(75) Inventors: Domenico Fanara, Wanze (BE); Jean Scouvart, Brussels (BE); Claire Poulain, Brussels (BE); Michel Deleers, Linkebeek (BE)

(73) Assignee: UCB Pharma, S.A., Brussels (BE)

( * ) Notice: Subject to any disclaimer, the term of this patent is extended or adjusted under 35 U.S.C. 154(b) by 832 days.

(21) Appl. No.: 10/599,451

(22) PCT Filed: Jul. 6, 2005

(86) PCT No.: PCT/EP2005/007340
§ 371 (c)(1),
(2), (4) Date: Jul. 18, 2007

(87) PCT Pub. No.: WO2006/005507
PCT Pub. Date: Jan. 19, 2006

(65) Prior Publication Data
US 2007/0275974 A1    Nov. 29, 2007

(30) Foreign Application Priority Data
Jul. 14, 2004   (EP) ................... 04016519

(51) Int. Cl.
*A61K 31/48* (2006.01)
(52) U.S. Cl.
USPC .................................................. 514/252.12
(58) Field of Classification Search
None
See application file for complete search history.

(56) References Cited

U.S. PATENT DOCUMENTS

| | | |
|---|---|---|
| 4,525,358 A | 6/1985 | Baltes et al. |
| 4,705,683 A | 11/1987 | Dettmar |
| 4,728,509 A | 3/1988 | Shimizu et al. |
| 5,368,852 A | 11/1994 | Umemoto et al. |
| 5,419,898 A | 5/1995 | Ikejiri |
| 5,504,113 A | 4/1996 | Lucero et al. |
| 5,891,913 A | 4/1999 | Sallmann et al. |
| 6,004,968 A | 12/1999 | Casey et al. |
| 6,258,814 B1 | 7/2001 | Martin |
| 6,319,927 B1 | 11/2001 | Martin |
| 6,432,961 B1 | 8/2002 | De Longueville et al. |
| 6,436,924 B2 | 8/2002 | Poppe et al. |
| 7,094,429 B2 | 8/2006 | Kiel et al. |
| 7,157,464 B2 | 1/2007 | Pennell et al. |
| 7,198,800 B1 | 4/2007 | Ko |
| 2004/0058896 A1* | 3/2004 | Dietrich et al. ............... 514/171 |
| 2009/0137645 A1 | 5/2009 | Zhang et al. |

FOREIGN PATENT DOCUMENTS

| | | |
|---|---|---|
| EP | 0 605 203 A | 7/1994 |
| EP | 0605203 A | 7/1994 |
| EP | 0605203 A2 | 7/1994 |
| WO | 2002/047689 A2 | 6/2002 |
| WO | WO 2004/004705 A | 1/2004 |
| WO | 2004/050094 A1 | 6/2004 |
| WO | 2005/107711 A2 | 11/2005 |

OTHER PUBLICATIONS

Doron et al.; "Antibacterial effect of parabens against planktonic and biofilm *Streptococcus sobrinus*"; 2001 International Journal of Antimicrobial Agents; 18: 575-578.*
Gilliland et al.; "The bactericidal activity of a methyl and propyl parabens combination: isothermal and non-isothermal studies"; 1992; Journal of Applied Bacteriology; 72: 252-257.*
Gilliland et al. "Kinetic evaluation of claimed synergistic paraben combinations using a factorial design"; 1992; Journal of Applied Bacteriology; 72: 258-261.*
Routledge et al.; "Some Alkyl Hydroxy Benzoate Preservatives (Parabens) Are Estrogenic"; 1998; Toxicology and Applied Pharmacology; 153: 12-19.*
Database WPI, Section Ch, Week 198551, Derwent Publications Ltd., London, GB; Class A96, AN 1985-319295, XP002309643, & JP 60 204712 A (SS Pharmaceutical KK), (Oct. 16, 1985) *abstract*.
Handbook of Pharmaceutical Manufacturing Formulations, Par Sarfaraz Niazi, CRC Press, 2004 (5 pages).
Formulation in Pharmacy Practices, 2nd edition, 2001 (2 pages).
Definition of Levo-Dromoran. Internet document http://www.rxlist.com/levo-dromoran-drug.htm, 1 sheet.
Remington the Science and Practice of Pharmacy, 21st ed., 2005, pp. 748-749.
Communication of a notice of opposition against European Application No. 05758582.0 dated Jun. 29, 2010 listing cited documents.
Kibbe A. H., "Handbook of Pharmaceutical Excipients", 3. edition 2000, American Pharmaceutical Association, pp. 340,450; ISBN: 0-917330-96-X.
Wang, D.Y., "Effect of cetirizine, levocetirizine, and dextrocetirizine on histamine-induced nasal response in healthy adult volunteers", Allergy 56 (2001), pp. 339-343; ISSN: 0105-4538.
Marketing authorization for Zodac R GTT in Slovakia.
Marketing authorization for Zodac R SIR in Slovakia.
Marketing authorization for Zodac R GTT in Czech Republic.
Marketing authorization for Zodac R SIR in Czech Republic.
Summary of product characteristics for Zodac R GTT.
Summary of product characteristics for Zodac R SIR.
Thomson Reuters Newport Premium: Launched Drug Forms Details.
Kibbe, Arthur H., "Handbook of Pharmaceutical Excipients", Third Edition 2000, American Pharmaceutical Association, pp. 340-343, 450-453.

\* cited by examiner

*Primary Examiner* — Timothy Thomas
*Assistant Examiner* — Rayna B Rodriguez
(74) *Attorney, Agent, or Firm* — McDonnell Boehnen Hulbert & Berghoff LLP

(57) ABSTRACT

The present invention relates to a liquid composition containing an active substance belonging to the family of substituted benzhydryl piperazines with reduced amounts of preservatives.

12 Claims, No Drawings

PHARMACEUTICAL COMPOSITION OF PIPERAZINE DERIVATIVES

The present invention relates to a liquid pharmaceutical composition containing an active substance such as cetirizine, levocetirizine and efletirizine.

A number of substances belonging to the family of substituted benzhydryl piperazines are known to be substances with useful pharmacological properties.

European Patent EP 58146, filed in the name of UCB, S.A., describes substituted benzhydryl piperazines having the general formula

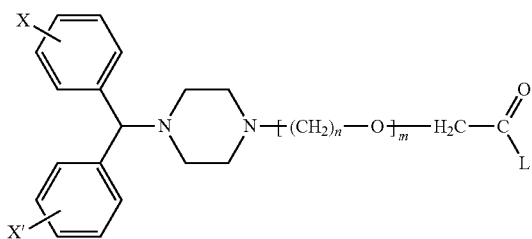

in which L stands for an —OH or —NH$_2$ group, X and X', taken separately, stand for a hydrogen atom, a halogen atom, a linear or branched alkoxy radical at $C_1$ or $C_4$, or a trifluoromethyl radical, m equals 1 or 2, n equals 1 or 2, as well as their pharmaceutically acceptable salts.

Of these compounds, 2-[2-[4-[(4-chlorophenyl)phenylmethyl]-1-piperazinyl]ethoxy]-acetic acid, also known under the name of cetirizine, and its dichlorohydrate are well known for their antihistaminic properties.

The active substances belonging to the family of substituted benzhydryl piperazines specifically include 2-[2-[4-[(4-chlorophenyl)phenylmethyl]-1-piperazinyl]ethoxy]-acetic acid (cetirizine), 2-[2-[4-[bis(4-fluorophenyl)methyl]-1-piperazinyl]ethoxy]acetic acid (efletirizine), their optically active isomers when applicable, as well as their pharmaceutically acceptable salts.

In the pharmaceutical filed, solutions and drops are generally produced as germ-free compositions during their production processes. However, once the seal of the containers is broken, and the pharmaceutical compositions are completely used over a period of time, these pharmaceutical compositions are continuously exposed to the risk of being contaminated by the microorganisms existing in the environment or the human body, each time the containers are used and their covers are opened or closed.

It has now surprisingly been found that the active substances belonging to the family of substituted benzhydryl piperazines possess a preservative effect in aqueous solutions.

The purpose of the invention concerns a liquid pharmaceutical composition containing an active substance belonging to the family of substituted benzhydryl piperazines chosen among cetirizine, levocetirizine and efletirizine, and a reduced amount of preservatives.

The present invention is based on the unexpected recognition that a pharmaceutical composition comprising an active substance belonging to the family of substituted benzhydryl piperazines and a reduced amount of preservatives is stable during a long period of time. Stability means the capacity to resists to microbial contamination.

The present invention encompasses a pharmaceutical composition comprising an active substance belonging to the family of substituted benzhydryl piperazines and an amount of parahydroxybenzoate esters used as preservatives less than 3 mg/ml of the composition, a normal concentration to preserve aqueous solutions.

The present invention encompasses a pharmaceutical composition comprising an active substance chosen among cetirizine, levocetirizine and efletirizine and at least one preservative, wherein the amount of preservative is in the case of parahydroxybenzoate esters more than 0 and less than 1.5 mg/ml of the composition, and in the case of other preservatives corresponds to the bactericidal effect of a parahydroxybenzoate esters concentration of more than 0 and less than 1.5 mg/ml.

Generally, the pharmaceutical composition of the invention is liquid and preferably aqueous.

In the pharmaceutical composition of the invention, the active substance is generally selected from the group of cetirizine, levocetirizine, efletirizine, and their pharmaceutically acceptable salts. Preferably, the active substance is selected from the group of cetirizine, levocetirizine, and their pharmaceutically acceptable salts.

The term "cetirizine" refers to the racemate of [2-[4-[(4 chlorophenyl)phenylmethyl]-1-piperazinyl]ethoxy]-acetic acid and its dihydrochloride salt which is well known as cetirizine dihydrochloride; its levorotatory and dextrorotatory enantiomers are known as levocetirizine and dextrocetirizine. Processes for preparing cetirizine, an individual optical isomer thereof or a pharmaceutically acceptable salt thereof have been described in European Patent 0 058 146, Great Britain Patent 2.225.320, Great Britain Patent 2.225.321, U.S. Pat. No. 5,478,941, European Patent application 0 601 028, European Patent Application 0 801 064 and International Patent Application WO 97/37982.

The term "levocetirizine" as used herein means the levorotatory enantiomer of cetirizine. More precisely, it means that the active substance comprises at least 90% by weight, preferably at least 95% by weight, of one individual optical isomer of cetirizine and at most 10% by weight, preferably at most 5% by weight, of the other individual optical isomer of cetirizine. Each individual optical isomer may be obtained by conventional means, i.e., resolution from the corresponding racemic mixture or by asymmetric synthesis. Each individual optical isomer may be obtained from its racemic mixture by using conventional means such as disclosed in British patent application No. 2,225,321. Additionally, each individual optical isomer can be prepared from the racemic mixture by enzymatic biocatalytic resolution, such as disclosed in U.S. Pat. Nos. 4,800,162 and 5,057,427.

The term "efletirizine" as used herein refers to 2-[2-[4-[bis (4-fluorophenyl)methyl]-1-piperazinyl]ethoxy]acetic acid. Efletirizine is encompassed within general formula I of European patent No. 58146, which relates to substituted benzhydrylpiperazine derivatives. Efletirizine has been found to possess excellent antihistaminic properties. It belongs to the pharmacological class of histamine $H_1$-receptor antagonists and shows in vitro high affinity and selectivity for $H_1$-receptors. It is useful as an antiallergic, and antihistaminic agent. Two pseudopolymorphic crystalline forms of efletirizine dihydrochloride, namely anhydrous efletirizine dihydrochloride and efletirizine dihydrochloride monohydrate, are described in the European patent No. 1 034 171, and another pseudopolymorphic form of efletirizine dihydrochloride is described in the international patent application WO 03/009849. Processes for preparing efletirizine or a pharmaceutically acceptable salt thereof have been described in European Patent 1 034 171, and in the international patent applications WO 97/37982 and WO 03/009849.

The term "pharmaceutically acceptable salts" as used herein refers not only to addition salts with pharmaceutically acceptable non-toxic organic and inorganic acids, such as acetic, citric, maleic, succinic, ascorbic, hydrochloric, hydrobromic, sulfuric, and phosphoric acids and the like, but also its metal salts (for example sodium or potassium salts) or ammonium salts, the amine salts and the aminoacid salts. The best results have been obtained with dihydrochloride salts.

By preservatives we understand a chemically substance that inhibits the development of microorganisms or, in an ideal instance, kills them; so antimicrobial agent able to limit or avoid the growth of microorganisms such as bacteria, yeast and moulds in a solution. Preservatives will comply with Eur P. and USP requirements: for a product incubated with a large number of bacteria and fungi, the preservative must kill and reduce a required amount of bacteria and fungi within a prescribed time period.

Examples of preservatives are p-hydroxybenzoate esters (methyl parahydroxybenzoate, ethyl parahydroxybenzoate, propyl parahydroxybenzoate, butyl parahydroxybenzoate, C1-C20 alkyl parahydroxybenzoate and their sodium salts), acrinol, methyl rosaniline chloride, benzalkonium chloride, benzethonium chloride, cetylpyridinium chloride, cetylpyrodium bromide, chlorohexidine, chlorohexidine acetate, benzylalcohol, alcohol, chlorobutanol, isopropanol, ethanol, thimerosal, phenol, sorbic acid, potassium and calcium sorbate, benzoic acid, potassium and calcium benzoate, sodium benzoate, calcium acetate, calcium disodium ethylenediaminetetraacetate, calcium propionate, calcium sorbate, diethyl pyrocarbonate, sulphur dioxide, sodium sulphite, sodium bisulfite, boric acid, sodium tetraborate, propionic acid, sodium and calcium propionate, sodium thiosulfate, or a mixture therefore. Generally, the preservative is selected from the group of thimerosal, chlorohexidine acetate, benzylalcohol, benzalkonium chloride, p-hydroxybenzoate esters (methyl parahydroxybenzoate, ethyl parahydroxybenzoate, propyl parahydroxybenzoate, butyl parahydroxybenzoate, C1-C20 alkyl parahydroxybenzoate or a mixture thereof. Preferably the preservative is selected from the group of methyl parahydroxybenzoate, ethyl parahydroxybenzoate, propyl parahydroxybenzoate, a mixture of methyl parahydroxybenzoate and ethyl parahydroxybenzoate or propyl parahydroxybenzoate, and a mixture of methyl parahydroxybenzoate and propyl parahydroxybenzoate. Best results have been obtained with a mixture of methyl parahydroxybenzoate and propyl parahydroxybenzoate in a ratio of 9/1 expressed in weight.

In a particular embodiment of the invention, the pharmaceutical composition contains an amount of p-hydroxybenzoate esters (methyl p-hydroxybenzoate/propyl p-hydroxybenzoate in a ratio of 9/1 expressed in weight) selected in the range of 0.0001 and 1.5 mg/ml of the composition. Preferably, it contains an amount selected in the range of 0.01 and 1.125 mg/ml. More preferably it contains an amount of preservatives selected in the range of 0.1 and 1 mg/ml.

In a particular embodiment of the invention, the pharmaceutical composition contains an amount of thimerosal selected in the range of 0.0001 and 0.05 mg/ml of the composition. Preferably, it contains an amount selected in the range of 0.005 and 0.035 mg/ml. More preferably it contains an amount of preservatives selected in the range of 0.007 and 0.025 mg/ml.

In a particular embodiment of the invention, the pharmaceutical composition contains an amount of chlorhexidine acetate selected in the range of 0.0001 and 0.05 mg/ml of the composition. Preferably, it contains an amount selected in the range of 0.005 and 0.035 mg/ml. More preferably it contains an amount of preservatives selected in the range of 0.007 and 0.025 mg/ml.

In a particular embodiment of the invention, the pharmaceutical composition contains an amount of benzylalcohol selected in the range of 0.0001 and 10 mg/mi of the composition. Preferably, it contains an amount selected in the range of 0.05 and 7.5 mg/ml. More preferably it contains an amount of preservatives selected in the range of 1 and 5 mg/ml.

In a particular embodiment of the invention, the pharmaceutical composition contains an amount of benzalkonium chloride selected in the range of 0.0001 and 0.05 mg/ml of the composition. Preferably, it contains an amount selected in the range of 0.005 and 0.035 mg/ml. More preferably it contains an amount of preservatives selected in the range of 0.01 and 0.025 mg/ml.

The amount of the selected preservative is defined by comparison with the amount of parahydroxybenzoate ester leading to the same preservative effect. The optimum amount of preservative used in the invention depends on its nature. The preferred amount of preservative is such that it gives the same preservative effect as an amount of parahydroxybenzoate ester in the range of 0.2 and 1.125 mg/ml of the pharmaceutical composition.

By patient, we understand children, adolescents and adults, preferably of 2 years old. The targeted patients are usually old from 2 years and more.

A preferred daily dosage provides from about 0.0005 mg to about 2 mg of levocetirizine or a pharmaceutically acceptable salt thereof, per kg of body weight per patient. A particularly preferred daily dosage is from about 0.001 to about 2 mg per kg of body weight per patient. The best results have been obtained with a daily dosage from about 0.005 to 1 mg per kg of body weight per patient. The dosage may be administered once per day of treatment, or divided into smaller dosages, for examples 1 to 4 times a day, and preferably 1 to 3 times a day, and administrated over about a 24 hours time period to reach a total given dosage. Best results have been obtained with an administration of a composition of the invention twice a day for infants; and 5 mg once a day for children and adults. The exact dosages in which the compositions are administrated can vary according to the type of use, the mode of use, the requirements of the patient, as determined by a skilled practitioner. The exact dosage for a patient may be specifically adapted by a skilled person in view of the severity of the condition, the specific formulation used, and other drugs which may be involved.

The pharmaceutical forms according to the present invention may be prepared according to conventional methods used by pharmacists. The forms can be administered together with other components or biologicaly active agents, pharmaceutically acceptable surfactants, excipients, carriers, diluents and vehicles.

The pharmaceutical compositions of the invention include any conventional therapeutical inert carrier. The pharmaceutical compositions can contain inert as well as pharmacodynamically active additives. Liquid compositions can for example take the form of a sterile solution which is miscible with water. Furthermore, substances conventionally used as preserving, stabilizing, moisture-retaining, and emulsifying agents as well as substances such as salts for varying the osmotic pressure, substances for varying pH such as buffers, and other additives can also be present. If desired an antioxidant can be included in the pharmaceutical compositions. Pharmaceutical acceptable excipients or carriers for compositions include saline, buffered saline, dextrose or water. Compositions may also comprise specific stabilizing agents such as sugars, including mannose and mannitol. Carrier substances and diluents can be organic or inorganic substances, for example water, gelatine, lactose, starch, gum arabic, polyalkylene glycol, cellulose compounds and the like. A prerequisite is that all adjuvants and substances used in the manufacture of the pharmaceutical compositions are non-toxic.

Pharmaceutical compositions can be administered by spray inhalation. Any conventional pharmaceutical composition for spray inhalation administration may be used. Another preferred mode of administration is by aerosol.

The pharmaceutical compositions according to the present invention may also be administered orally. They may also be administered by nasal instillation, aerosols. The pharmaceutical compositions which can be used for oral administration is liquid, for example, in the form of solutions, syrups, drops and the like.

The pharmaceutical forms, such as drops, nasal drops, eye drops and ear drops are prepared by conventional pharmaceutical methods. The compounds of the present invention are mixed with a solid or liquid, non-toxic and pharmaceutically acceptable carrier and possibly also mixed with a dispersing agent, a stabilizing agent and the like. If appropriate, it is also possible to add sweeteners, coloring agents and the like.

Preferably, the pharmaceutical composition of the invention is administered in traditional form for oral administration, as oral liquid preparation such as syrup.

Best results have been obtained with an oral dosage form, in particular liquid formulations such as syrup for children.

An advantage of the invention is that reducing the concentration of the preservative leads to a reduction of the risk of an allergic reaction in sensitive patients.

Another advantage of the invention is the ability to make easier the manufacturing process avoiding the solubilization of important amounts of preservatives not freely soluble in water.

The invention is further defined by reference to the following examples.

EXAMPLE 1

Preservative Effect of Cetirizine

An oral solution and drops containing cetirizine are prepared. The compositions are given in table 1.

TABLE 1

| Cetirizine compositions | | |
| --- | --- | --- |
| | Oral solution | Drops |
| Cetirizine hydrochloride (mg) | 1 | 10 |
| Sorbitol sol. At 70% (mg) | 450 | — |
| Glycerine (mg) | 200 | 250 |
| Propyleneglycol (mg) | 50 | 350 |
| Sodium saccharinate (mg) | 1 | 10 |
| Banana flavour (mg) | 0.1754 | — |
| Sodium acetate (mg) | 4.2 | 10 |
| Acetic acid | ad pH 5 | ad pH 5 |
| Purified water (ml) | ad 1 | ad 1 |

The antimicrobial preservative effectiveness tests are realized according to the European Pharmacopoeia (Chap. 5.1.3.). Samples of the oral solution and the drops are inoculated with bacterial and yeast suspensions of *Pseudomonas aeruginosa* ATCC 9027, *Escherichia Coli* ATCC 8739, *Staphylococcus aureus* ATC C6538, *Candida albicans* ATCC10231 and *Aspergillus niger* ATCC16404. The number of viable microorganisms per ml of preparations under test are determined. The results are given in tables 2 and 3.

TABLE 2

| Microbial content in inoculated sample of the oral solution | | | | | |
| --- | --- | --- | --- | --- | --- |
| Time (days) | *Pseudomonas aeruginosa* | *Escherichia coli* | *Staphylococcus aureus* | *Candida albicans* | *Aspergillus niger* |
| Inoculum | $5.5 \times 10^5$ | $4.6 \times 10^5$ | $4.0 \times 10^5$ | $3.7 \times 10^5$ | $2.3 \times 10^6$ |
| 0 | $4.9 \times 10^5$ | $4.7 \times 10^5$ | $3.1 \times 10^5$ | $2.6 \times 10^5$ | $1.7 \times 10^6$ |
| 7 | <100 | <100 | <100 | <100 | $4.8 \times 10^5$ |
| 14 | <1 | <1 | <1 | 2 | $8.2 \times 10^3$ |
| 21 | <1 | <1 | <1 | <1 | $5.5 \times 10^3$ |
| 28 | <1 | <1 | <1 | <1 | $5.0 \times 10^3$ |

TABLE 3

| Microbial content in inoculated sample of the drops | | | | | |
| --- | --- | --- | --- | --- | --- |
| Time (days) | *Pseudomonas aeruginosa* | *Escherichia coli* | *Staphylococcus aureus* | *Candida albicans* | *Aspergillus niger* |
| Inoculum | $4.0 \times 10^5$ | $3.4 \times 10^5$ | $3.6 \times 10^5$ | $3.5 \times 10^5$ | $1.8 \times 10^6$ |
| 0 | $3.5 \times 10^5$ | $3.8 \times 10^5$ | $2.2 \times 10^5$ | $2.6 \times 10^5$ | $1.6 \times 10^6$ |
| 7 | <100 | <100 | <100 | <100 | $<10^4$ |
| 14 | <1 | <1 | <1 | <1 | <100 |
| 21 | <1 | <1 | <1 | <1 | <1 |
| 28 | <1 | <1 | <1 | <1 | <1 |

In both cases, a rapid disappearance of *Pseudomonas aeruginosa, Escherichia Coli, Staphylococcus aureus* and *Candida albicans* is observed in the inoculated samples.

For *Aspergillus niger*, the number of viable spores is significantly reduced in the oral solution while a rapid disappearance is observed in the drops.

EXAMPLE 2

Preservative Effect of Levocetirizine

An oral solution and drops containing levocetirizine are prepared. The compositions are given in table 4.

TABLE 4

| Levocetirizine compositions | | |
| --- | --- | --- |
| | Oral solution | Drops |
| Levocetirizine hydrochloride (mg) | 0.5 | 5 |
| Maltitol-Lycasin 80-55 (mg) | 400 | — |
| Glycerine 85% (mg) | 235.2 | 294.1 |
| Propyleneglycol (mg) | — | 350 |
| Sodium saccharinate (mg) | 0.5 | 10 |
| Tutti frutti flavour (mg) | 0.15 | — |
| Sodium acetate (mg) | 3.4 | 5.7 |
| Acetic acid (mg) | 0.5 | 0.53 |
| Purified water (ml) | ad 1 | ad 1 |

The antimicrobial preservative effectiveness tests are realized according to the European Pharmacopoeia (Chap. 5.1.3.). Samples of the oral solution and the drops are inoculated with bacterial and yeast suspensions of *Pseudomonas aeruginosa* ATCC 9027, *Escherichia Coli* ATCC 8739, *Staphylococcus aureus* ATC C6538, *Candida albicans* ATCC10231 and *Aspergillus niger* ATCC16404. The number of viable microorganisms per ml of preparations under test is determined. The results are given in tables 5 and 6.

TABLE 5

Microbial content in inoculated sample of the oral solution

| Time (days) | Pseudomonas aeruginosa | Escherichia coli | Staphylococcus aureus | Candida albicans | Aspergillus niger |
|---|---|---|---|---|---|
| Inoculum | $3.6 \times 10^5$ | $1.7 \times 10^5$ | $2.7 \times 10^5$ | $3.4 \times 10^5$ | $1.7 \times 10^6$ |
| 0 | $3.2 \times 10^5$ | $1.8 \times 10^5$ | $3.5 \times 10^5$ | $3.9 \times 10^5$ | $1.6 \times 10^6$ |
| 7 | 150 | <100 | <100 | $2.8 \times 10^4$ | $1.0 \times 10^6$ |
| 14 | <1 | <1 | <1 | $1.4 \times 10^4$ | $4.8 \times 10^5$ |
| 21 | <1 | <1 | <1 | $2.6 \times 10^2$ | $2.2 \times 10^5$ |
| 28 | <1 | <1 | <1 | $6.2 \times 10^3$ | $5.3 \times 10^5$ |

TABLE 6

Microbial content in inoculated sample of the drops

| Time (days) | Pseudomonas aeruginosa | Escherichia coli | Staphylococcus aureus | Candida albicans | Aspergillus niger |
|---|---|---|---|---|---|
| Inoculum | $3.6 \times 10^5$ | $1.7 \times 10^5$ | $2.7 \times 10^5$ | $3.4 \times 10^5$ | $1.7 \times 10^6$ |
| 0 | $3.2 \times 10^5$ | $1.5 \times 10^5$ | $3.1 \times 10^5$ | $1.8 \times 10^5$ | $1.7 \times 10^6$ |
| 7 | <100 | <100 | <100 | <100 | $9.0 \times 10^4$ |
| 14 | <1 | <1 | <1 | <1 | <1000 |
| 21 | <1 | <1 | <1 | <1 | <1 |
| 28 | <1 | <1 | <1 | <1 | <1 |

In both cases, a rapid disappearance of *Pseudomonas aeruginosa*, *Escherichia Coli*, *Staphylococcus aureus* is observed in the inoculated samples. A disappearance of *Candida albicans* and *Aspergillus niger* is also observed in the drops.

EXAMPLE 3

Efficacy of Antimicrobial Preservation of Cetirizine Aqueous Solutions by p-hydroxbenzoate Esters Oral solutions and drops containing cetirizine according to example 1 but also containing mixtures of p-hydroxybenzoate esters (methyl p-hydroxybenzoate/propyl p-hydroxybenzoate in a ratio of 9/1 expressed in weight) are prepared. The total amounts of p-hydroxybenzoate esters are 0.15 mg/ml, 0.45 mg/ml, 0.75 mg/ml and 1.05 mg/ml. The efficacy of antimicrobial preservation of these solutions and drops is determined according to the European Pharmacopoeia (Chap. 5.1.3.). The results of the tests are given in tables 7 to 14.

TABLE 7

Microbial content in inoculated sample of the oral solution containing 0.15 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $5.5 \times 10^5$ | $4.6 \times 10^5$ | $4.0 \times 10^5$ | $3.7 \times 10^5$ | $2.3 \times 10^6$ |
| 0 | $5.1 \times 10^5$ | $4.5 \times 10^5$ | $3.0 \times 10^5$ | $4.0 \times 10^5$ | $4.1 \times 10^6$ |
| 14 | <1 | <1 | <1 | <1 | $9.1 \times 10^3$ |
| 28 | <1 | <1 | <1 | <1 | 750 |

TABLE 8

Microbial content in inoculated sample of the oral solution containing 0.45 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $5.5 \times 10^5$ | $4.6 \times 10^5$ | $4.0 \times 10^5$ | $3.7 \times 10^5$ | $2.3 \times 10^6$ |
| 0 | $5.2 \times 10^5$ | $4.9 \times 10^5$ | $3.3 \times 10^5$ | $2.9 \times 10^5$ | $1.2 \times 10^6$ |
| 14 | <1 | <1 | <1 | <1 | <100 |
| 28 | <1 | <1 | <1 | <1 | 2 |

TABLE 9

Microbial content in inoculated sample of the oral solution containing 0.75 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $5.5 \times 10^5$ | $4.6 \times 10^5$ | $4.0 \times 10^5$ | $3.7 \times 10^5$ | $2.3 \times 10^6$ |
| 0 | $3.9 \times 10^5$ | $4.4 \times 10^5$ | $4.0 \times 10^5$ | $1.9 \times 10^5$ | $1.9 \times 10^6$ |
| 14 | <1 | <1 | <1 | <1 | <100 |
| 28 | <1 | <1 | <1 | <1 | <1 |

TABLE 10

Microbial content in inoculated sample of the oral solution containing 1.05 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $5.5 \times 10^5$ | $4.6 \times 10^5$ | $4.0 \times 10^5$ | $3.7 \times 10^5$ | $2.3 \times 10^6$ |
| 0 | $3.3 \times 10^5$ | $4.1 \times 10^5$ | $3.1 \times 10^5$ | $1.4 \times 10^5$ | $1.2 \times 10^6$ |
| 14 | <1 | <1 | <1 | <1 | <100 |
| 28 | <1 | <1 | <1 | <1 | <1 |

TABLE 11

Microbial content in inoculated sample of the drops containing 0.15 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $4.0 \times 10^5$ | $3.4 \times 10^5$ | $3.6 \times 10^5$ | $3.5 \times 10^5$ | $1.8 \times 10^6$ |
| 0 | $4.3 \times 10^5$ | $4.0 \times 10^5$ | $2.0 \times 10^5$ | $2.5 \times 10^5$ | $1.5 \times 10^6$ |
| 14 | <1 | <1 | <1 | <1 | <100 |
| 28 | <1 | <1 | <1 | <1 | <1 |

TABLE 12

Microbial content in inoculated sample of the drops containing 0.45 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $4.0 \times 10^5$ | $3.4 \times 10^5$ | $3.6 \times 10^5$ | $3.5 \times 10^5$ | $1.8 \times 10^6$ |
| 0 | $3.6 \times 10^5$ | $3.6 \times 10^5$ | $1.7 \times 10^5$ | $2.1 \times 10^5$ | $1.4 \times 10^6$ |
| 14 | <1 | <1 | <1 | <1 | <100 |
| 28 | <1 | <1 | <1 | <1 | <1 |

TABLE 13

Microbial content in inoculated sample of the drops containing 0.75 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $4.0 \times 10^5$ | $3.4 \times 10^5$ | $3.6 \times 10^5$ | $3.5 \times 10^5$ | $1.8 \times 10^6$ |
| 0 | $4.1 \times 10^5$ | $3.6 \times 10^5$ | $2.6 \times 10^5$ | $2.5 \times 10^5$ | $1.6 \times 10^6$ |
| 14 | <1 | <1 | <1 | <1 | <100 |
| 28 | <1 | <1 | <1 | <1 | <1 |

TABLE 14

Microbial content in inoculated sample of the drops containing 1.05 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $4.0 \times 10^5$ | $3.4 \times 10^5$ | $3.6 \times 10^5$ | $3.5 \times 10^5$ | $1.8 \times 10^6$ |
| 0 | $3.9 \times 10^5$ | $3.7 \times 10^5$ | $2.8 \times 10^5$ | $2.2 \times 10^5$ | $1.3 \times 10^6$ |
| 14 | <1 | <1 | <1 | <1 | <100 |
| 28 | <1 | <1 | <1 | <1 | <1 |

In all cases, the disappearance of *Pseudomonas aeruginosa*, *Escherichia Coli*, *Staphylococcus aureus* and *Candida albicans* is observed in the inoculated samples. For *Aspergillus niger*, the number of viable spores is significantly reduced in the oral solution while a rapid disappearance is observed in the drops.

In all cases the recommended efficacy criteria are achieved.

EXAMPLE 4

Efficacy of Antimicrobial Preservation of Levocetirizine Aqueous Solutions by p-hydroxybenzoate Esters Oral solutions and drops containing levocetirizine according to example 2 but also containing mixtures of p-hydroxybenzoate esters (methyl p-hydroxybenzoate/propyl p-hydroxybenzoate in a ratio of 9/1 expressed in weight) are prepared. The total amounts of p-hydroxybenzoate esters are 0.375 mg/ml, 0.75 mg/ml and 1.125 mg/ml. The efficacy of antimicrobial preservation of these solutions and drops is determined according to the European Pharmacopoeia (Chap. 5.1.3.). The results of the tests are given in tables 15 to 20.

TABLE 15

Microbial content in inoculated sample of the oral solution containing 0.375 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $3.6 \times 10^5$ | $1.7 \times 10^5$ | $2.7 \times 10^5$ | $3.4 \times 10^5$ | $1.7 \times 10^6$ |
| 0 | $3.7 \times 10^5$ | $1.3 \times 10^5$ | $2.8 \times 10^5$ | $3.8 \times 10^5$ | $1.6 \times 10^6$ |
| 14 | <1 | <1 | <1 | $1.7 \times 10^4$ | $1.6 \times 10^5$ |
| 28 | <1 | <1 | <1 | <1 | <100 |

TABLE 16

Microbial content in inoculated sample of the oral solution containing 0.75 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $3.6 \times 10^5$ | $1.7 \times 10^5$ | $2.7 \times 10^5$ | $3.4 \times 10^5$ | $1.7 \times 10^6$ |
| 0 | $3.5 \times 10^5$ | $1.6 \times 10^5$ | $2.4 \times 10^5$ | $3.4 \times 10^5$ | $1.6 \times 10^6$ |
| 14 | <1 | <1 | <1 | $5.5 \times 10^2$ | $1.4 \times 10^4$ |
| 28 | <1 | <1 | <1 | <1 | <1 |

TABLE 17

Microbial content in inoculated sample of the oral solution containing 1.125 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $3.6 \times 10^5$ | $1.7 \times 10^5$ | $2.7 \times 10^5$ | $3.4 \times 10^5$ | $1.7 \times 10^6$ |
| 0 | $3.9 \times 10^5$ | $1.2 \times 10^5$ | $3.0 \times 10^5$ | $3.5 \times 10^5$ | $1.4 \times 10^6$ |
| 14 | <1 | <1 | <1 | <10 | <1000 |
| 28 | <1 | <1 | <1 | <1 | <1 |

TABLE 18

Microbial content in inoculated sample of the drops containing 0.375 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $3.6 \times 10^5$ | $1.7 \times 10^5$ | $2.7 \times 10^5$ | $3.4 \times 10^5$ | $1.7 \times 10^6$ |
| 0 | $3.1 \times 10^5$ | $1.2 \times 10^5$ | $2.6 \times 10^5$ | $1.7 \times 10^5$ | $1.8 \times 10^6$ |
| 14 | <1 | <1 | <1 | <1 | <1000 |
| 28 | <1 | <1 | <1 | <1 | <1 |

TABLE 19

Microbial content in inoculated sample of the drops containing 0.75 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $3.6 \times 10^5$ | $1.7 \times 10^5$ | $2.7 \times 10^5$ | $3.4 \times 10^5$ | $1.7 \times 10^6$ |
| 0 | $3.1 \times 10^5$ | $1.0 \times 10^5$ | $3.0 \times 10^5$ | $1.8 \times 10^5$ | $1.4 \times 10^6$ |
| 14 | <1 | <1 | <1 | <1 | <1000 |
| 28 | <1 | <1 | <1 | <1 | <1 |

TABLE 20

Microbial content in inoculated sample of the drops containing 1.125 mg/ml of p-hydroxybenzoate esters

| Time (days) | Pseudomonas aeruginosa | Escherichia coli | Staphylococcus aureus | Candida albicans | Aspergillus niger |
|---|---|---|---|---|---|
| Inoculum | $3.6 \times 10^5$ | $1.7 \times 10^5$ | $2.7 \times 10^5$ | $3.4 \times 10^5$ | $1.7 \times 10^6$ |
| 0 | $2.9 \times 10^5$ | $6.9 \times 10^4$ | $2.7 \times 10^5$ | $5.0 \times 10^4$ | $1.5 \times 10^6$ |
| 14 | <1 | <1 | <1 | <1 | <1000 |
| 28 | <1 | <1 | <1 | <1 | <1 |

In all cases, the disappearance of *Pseudomonas aeruginosa, Escherichia Coli, Staphylococcus aureus* and *Candida albicans* is observed in the inoculated samples.

For *Aspergillus niger*, the number of viable spores is significantly reduced in the oral solution while a rapid disappearance is observed in the drops. In all cases the recommended efficacy criteria are achieved.

EXAMPLE 5

Nasal Solution Containing Cetirizine and Benzalkonium Chloride

A solution containing cetirizine is prepared. The composition is given in table 21.

TABLE 21

| Cetirizine composition | |
| --- | --- |
|  | Nasal solution |
| Cetirizine hydrochloride (mg) | 10 |
| Monobasic sodium phosphate (mg) | 10.6 |
| Dibasic sodium phosphate (mg) | 29 |
| Benzalkonium chloride (mg) | 0.025 |
| Purified water (ml) | ad 1 |

The efficacy of antimicrobial preservation of this solution is determined according to the European Pharmacopoeia (Chap. 5.1.3.). The recommended efficacy criteria are achieved.

EXAMPLE 6

Nasal Solution Containing Efletirizine and p-hydroxybenzoate Esters

A solution containing efletirizine is prepared. The composition is given in table 22.

TABLE 22

| Efletirizine composition | |
| --- | --- |
|  | Nasal solution |
| Efletirizine hydrochloride (mg) | 6 |
| Hydroxypropylmethylcellulose (mg) | 5 |
| Monobasic sodium phosphate (mg) | 8.1 |
| Dibasic sodium phosphate (mg) | 6.3 |
| Edeteate disodium (mg) | 0.5 |
| Sodium chloride (mg) | 1.93 |
| Sodium hydroxide | ad pH 6.5 |
| p-hydroxybenzoate esters (mg) | 0.375 |
| Purified water (ml) | ad 1 |

The efficacy of antimicrobial preservation of this solution is determined according to the European Pharmacopoeia (Chap. 5.1.3.). The recommended efficacy criteria are achieved.

EXAMPLE 7

Oral Solutions and Drops Containing Levocetirizine and Benzylalcohol

An oral solution and drops containing levocetirizine are prepared. The compositions are given in table 23.

TABLE 23

| Levocetirizine compositions | | |
| --- | --- | --- |
|  | Oral solution | Drops |
| Levocetirizine hydrochloride (mg) | 0.5 | 5 |
| Maltitol-Lycasin 80-55 (mg) | 400 | — |
| Glycerine 85% (mg) | 235.2 | 294.1 |
| Propyleneglycol (mg) | — | 350 |
| Sodium saccharinate (mg) | 0.5 | 10 |
| Tutti frutti flavour (mg) | 0.15 | — |
| Sodium acetate (mg) | 3.4 | 5.7 |
| Acetic acid (mg) | 0.5 | 0.53 |
| Benzylalcohol (mg) | 5.0 | 5.0 |
| Purified water (ml) | ad 1 | ad 1 |

The antimicrobial preservative effectiveness tests are realized according to the European Pharmacopoeia (Chap. 5.1.3.). In all cases the recommended efficacy criteria are achieved.

EXAMPLE 8

Oral Solutions and Drops Containing Efletirizine

An oral solution and drops containing efletirizine are prepared. The compositions are given in table 24.

TABLE 24

| Efletirizine compositions | | |
| --- | --- | --- |
|  | Oral solution | Drops |
| Efletirizine hydrochloride (mg) | 1 | 10 |
| Maltitol-Lycasin 80-55 (mg) | 400 | — |
| Glycerine 85% (mg) | 235.2 | 294.1 |
| Propyleneglycol (mg) | — | 350 |
| Sodium saccharinate (mg) | 0.5 | 10 |
| Tutti frutti flavour (mg) | 0.15 | — |
| Sodium acetate (mg) | 4.2 | 10 |
| Acetic acid (mg) | ad pH 5 | ad pH 5 |
| p-hydroxybenzoate esters (mg) | 0.375 | 0.375 |
| Purified water (ml) | ad 1 | ad 1 |

The antimicrobial preservative effectiveness tests are realized according to the European Pharmacopoeia (Chap. 5.1.3.). In all cases the recommended efficacy criteria are achieved.

EXAMPLE 9

Eye Drops Containing Efletirizine and Thimerosal, Chlorhexidine Acetate and p-hydroxybenzoate Esters Three formulations of eye drops containing efletirizine are prepared. The compositions are given in table 25.

TABLE 25

| Efletirizine compositions | | | |
| --- | --- | --- | --- |
|  | Eye drops | | |
| Efletirizine hydrochloride (mg) | 10 | 10 | 10 |
| Boric acid (mg) | 20 | 20 | 20 |
| Sodium hydroxide | ad pH 7 | ad pH 7 | ad pH 7 |
| Thimerosal (mg) | 0.05 | — | — |
| Chlorhexidine acetate (mg) | — | 0.05 | — |
| p-hydroxybenzoate esters (mg) | — | — | 0.375 |
| Purified water (ml) | ad 1 | ad 1 | ad 1 |

The antimicrobial preservative effectiveness tests are realized according to the European Pharmacopoeia (Chap. 5.1.3.). In all cases the recommended efficacy criteria are achieved.

The invention claimed is:

1. A liquid pharmaceutical composition comprising (i) levocetirizine or a pharmaceutically acceptable salt of levocetirizine, and (ii) a preservative mixture consisting essentially of a mixture of methyl parahydroxybenzoate and propyl parahydroxybenzoate in a ratio of 9/1 expressed in weight, said mixture being present in an amount of more than 0 and up to 0.75 mg/ml of the composition, wherein said composition is substantially free of bacteria.

2. The liquid pharmaceutical composition according to claim 1, wherein the composition is aqueous.

3. The liquid pharmaceutical composition according to claim 1, wherein the amount of the p-hydroxybenzoate esters is in the range of 0.0001 to 0.75 mg/ml of the composition.

4. The liquid pharmaceutical composition according to claim 1, wherein the composition is in the form of oral solutions, nasal drops, eye drops or ear drops.

5. The liquid pharmaceutical composition according to claim 1, wherein the pharmaceutically acceptable salt of levocetirizine is a hydrochloride salt.

6. The liquid pharmaceutical composition according to claim 5, wherein the hydrochloride salt of levocetirizine is present in amount of 0.5 mg/ml and the mixture of methyl p-hydroxybenzoate and propyl p-hydroxybenzoate is present in amount of 0.75 mg/ml.

7. The liquid pharmaceutical composition according to claim 1, which composition comprises levocetirizine or a pharmaceutically acceptable salt that is at least 95% by weight of the levorotatory enantiomer of cetirizine.

8. A method of making a liquid pharmaceutical composition according to claim 1 comprising mixing levocetirizine or a pharmaceutically acceptable salt thereof with a mixture of methyl p-hydroxybenzoate and propyl p-hydroxybenzoate, wherein the methyl p-hydroxybenzoate and propyl p-hydroxybenzoate are present in a ratio of 9:1.

9. The method according to claim 8, comprising mixing a pharmaceutically acceptable salt of levocetirizine with a mixture of methyl p-hydroxybenzoate and propyl p-hydroxybenzoate, wherein the methyl p-hydroxybenzoate and propyl p-hydroxybenzoate are present in a ratio of 9:1.

10. The method according to claim 9, wherein the pharmaceutically acceptable salt of levocetirizine is a hydrochloride salt.

11. The composition of claim 1, wherein the composition is in the form of an oral solution comprising 0.50 mg/ml levocetirizine dihydrochloride, 0.675 mg/ml methyl p-hydroxybenzoate, and 0.075 mg/ml propyl p-hydroxybenzoate.

12. The composition of claim 1, wherein the composition is in the form of a solution of oral drops comprising 5.0 mg/ml levocetirizine dihydrochloride, 0.3375 mg/ml methyl p-hydroxybenzoate, and 0.0375 mg/ml propyl p-hydroxybenzoate.

* * * * *

(12) INTER PARTES REVIEW CERTIFICATE (2244th)
United States Patent
Fanara et al.

(10) Number: US 8,633,194 K1
(45) Certificate Issued: Aug. 16, 2021

(54) PHARMACEUTICAL COMPOSITION OF PIPERAZINE DERIVATIVES

(75) Inventors: Domenico Fanara; Jean Scouvart; Claire Poulain; Michel Deleers

(73) Assignee: UCB PHARMA, S.A.

Trial Number:

IPR2019-00400 filed Dec. 13, 2018

Inter Partes Review Certificate for:

Patent No.: 8,633,194
Issued: Jan. 21, 2014
Appl. No.: 10/599,451
Filed: Jul. 18, 2007

The results of IPR2019-00400 are reflected in this inter partes review certificate under 35 U.S.C. 318(b).

INTER PARTES REVIEW CERTIFICATE
U.S. Patent 8,633,194 K1
Trial No. IPR2019-00400
Certificate Issued Aug. 16, 2021

AS A RESULT OF THE INTER PARTES REVIEW PROCEEDING, IT HAS BEEN DETERMINED THAT:

Claims 1-11 are found patentable.

\* \* \* \* \*